(12) United States Patent
Penhasi

(10) Patent No.: US 7,410,498 B2
(45) Date of Patent: Aug. 12, 2008

(54) POLYMERIC STENTS AND OTHER SURGICAL ARTICLES

(75) Inventor: Adel Penhasi, Holon (IL)

(73) Assignee: Pentech Medical Devices Ltd., Holon (IL)

(*) Notice: Subject to any disclaimer, the term of this patent is extended or adjusted under 35 U.S.C. 154(b) by 546 days.

(21) Appl. No.: 10/312,712

(22) PCT Filed: Jun. 26, 2001

(86) PCT No.: PCT/IL01/00579

§ 371 (c)(1),
(2), (4) Date: Dec. 30, 2002

(87) PCT Pub. No.: WO02/00092

PCT Pub. Date: Jan. 3, 2002

(65) Prior Publication Data

US 2003/0208259 A1    Nov. 6, 2003

(30) Foreign Application Priority Data

Jun. 29, 2000    (IL)    ................................. 137090

(51) Int. Cl.
*A61F 2/06*    (2006.01)

(52) U.S. Cl. ..................... 623/1.22; 623/1.44

(58) Field of Classification Search ............... 623/1.15, 623/1.1, 1.16, 1.19, 1.22
See application file for complete search history.

(56) References Cited

U.S. PATENT DOCUMENTS

| | | | |
|---|---|---|---|
| 4,403,985 A | 9/1983 | Boretos | |
| 4,784,639 A | 11/1988 | Patel | |
| 4,826,945 A | 5/1989 | Cohn et al. | |
| 4,861,830 A * | 8/1989 | Ward, Jr. | 525/92 A |
| 5,085,629 A | 2/1992 | Goldberg | |
| 5,163,952 A | 11/1992 | Froix | |
| 5,304,326 A | 4/1994 | Goto et al. | |
| 5,383,928 A | 1/1995 | Scott et al. | |
| 5,453,099 A | 9/1995 | Karakelle et al. | |
| 5,464,450 A | 11/1995 | Buscemi et al. | |
| 5,498,238 A | 3/1996 | Shapland et al. | |
| 5,510,077 A | 4/1996 | Dinh et al. | |
| 5,527,337 A | 6/1996 | Stack et al. | |
| 5,554,147 A | 9/1996 | Batich | |
| 5,554,182 A | 9/1996 | Dinh et al. | |

(Continued)

FOREIGN PATENT DOCUMENTS

EP    0 608 139 A1    7/1994

(Continued)

*Primary Examiner*—Corrine McDermott
*Assistant Examiner*—Cheryl Miller
(74) *Attorney, Agent, or Firm*—Nixon & Vanderhye P.C.

(57) ABSTRACT

A biocompatible non-memory expandable polymeric article selected from stents, implantable prostheses, catheters, other surgical articles and sealants for implantable prostheses, and which is at least in part biodegradable and includes a combination where hollow cylindrical element (2) is depicted in cutaway form to reveal helical element (4), terminated schematically at (6) and where a combination of at least one thermoplastic elastomeric component and at least one thermoplastic non-elastomeric component, the article being either porous articles or having the potential to become porous by action of body fluids in situ), the thermoplastic non-elastomeric component being present in such an amount as will provide mechanical strength and rigidity to the article when in an expanded mode.

3 Claims, 2 Drawing Sheets

U.S. PATENT DOCUMENTS

| | | | |
|---|---|---|---|
| 5,578,075 A * | 11/1996 | Dayton | 623/1.15 |
| 5,591,227 A | 1/1997 | Dinh et al. | |
| 5,603,722 A | 2/1997 | Phan et al. | |
| 5,607,467 A | 3/1997 | Froix | |
| 5,725,547 A | 3/1998 | Chuter | |
| 5,783,633 A * | 7/1998 | Sperling et al. | 525/131 |
| 5,811,447 A | 9/1998 | Kunz et al. | |
| 5,843,172 A | 12/1998 | Yan | |
| 5,954,706 A | 9/1999 | Sahatjian | |
| 5,972,027 A | 10/1999 | Johnson | |
| 5,980,551 A | 11/1999 | Summers et al. | |
| 6,013,099 A | 1/2000 | Dinh et al. | |
| 6,027,516 A | 2/2000 | Kolobow et al. | |
| 6,139,573 A * | 10/2000 | Sogard et al. | 623/1.13 |
| 6,261,316 B1 * | 7/2001 | Shaolian et al. | 623/1.11 |
| 6,605,111 B2 * | 8/2003 | Bose et al. | 623/1.18 |
| 6,626,939 B1 * | 9/2003 | Burnside et al. | 623/1.38 |
| 6,699,276 B2 * | 3/2004 | Sogard et al. | 623/1.13 |
| 2002/0169499 A1 * | 11/2002 | Zilla et al. | 623/1.15 |

FOREIGN PATENT DOCUMENTS

| | | | |
|---|---|---|---|
| EP | 0608139 A1 * | 7/1994 | |
| WO | WO 9942147 A1 | 2/1999 | |

* cited by examiner

POLYMERIC STENTS AND OTHER SURGICAL ARTICLES

This application claims the benefit of application 137090, in the Israeli Patent Office on Jun. 29, 2000, the disclosure of which is incorporated herein by reference.

FIELD OF THE INVENTION

The present invention relates to a polymeric stent and other surgical articles and sealants.

BACKGROUND OF THE INVENTION

Translumenal angioplasty is a technique of dilating blocked blood vessels from the inside, thus avoiding the need for more extensive surgical intervention. In balloon angioplasty a deflated balloon catheter is placed across the narrowed segment of the artery and then the balloon is inflated so as to transmit circumferential pressure and compress the plaque. This procedure more or less normalizes the internal lumenal size, following which natural healing generally occurs over a period of weeks or months. Even where a laser technique is used to evaporate a plaque blockage and create a channel, supplemental balloon dilatation is often advisable, in order to achieve an adequate internal lumenal size. In many cases it may be desirable, in order to expand the narrowed lumen and to maintain the opening, to inflate the balloon catheter while inside a stent (tube or coil), which provides a mechanical scaffolding and prevents the possible complete blockage of the artery that may occur due to unexpected tear with balloon angioplasty. The use of stent angioplasty, when considered appropriate, improves the chances of success, both immediately and on a long-term basis.

In recent years, the realization that the use of stents may be medically advantageous has led to a great increase in patent activity, in this field. A variety of stents, both metal and polymeric (or a combination of both) as well as stents in cylindrical and helical configurations (see e.g., U.S. Pat. No. 6,027,516 (Kolobow et al.)), have been proposed.

Methods for the manufacture of polymeric stents, as e.g., by extruding or molding operations, are by now well-known (see e.g. U.S. Pat. No. 5,085,629 (Goldberg), U.S. Pat. No. 5,510,077 (Dinh et al.), U.S. Pat. No. 5,527,337 (Stack et al.) and U.S. Pat. No. 5,972,027 (Johnson). Consequently, current research efforts appear to be directed to particular structures or compositions imparting desired properties to such stents, rather than to methods of manufacture per se.

One approach to the subject of polymeric stents has been to make an expandable stent with a memory. Thus, U.S. Pat. Nos. 5,163,952 and 5,607,467 (Froix) describe a cylindrical stent with a predetermined diameter and a memory of greater diameter, whereby on application of certain stimuli (heat, liquid absorption or pH change) the stent attempts to assume the greater diameter. Examples of polymers said to exhibit such properties are mainly copolymers of various methacrylates.

WO 9942147A1 (Langer et al.) also discloses shape memory polymer compositions, which are at least in part biodegradable. The compositions may comprise block copolymers containing both hard and soft segments, of which at least one segment is thermoplastic, or may utilize crosslinked sift segments in absence of hard segments. In one example, the hard segment was a hydroxy-terminated oligoglycolate, and the soft segment was a hydroxy-terminated oligolactate/glycolate or a poly(caprolactone)diol, linked by reaction with an alkanediisocyanate; in another example, thermoset poly(caprolactone)dimethacrylates were prepared. This document mentions stents as one of numerous proposed applications of the disclosed compositions, but gives no details as to how this might be affected in practice.

Polymeric stents with a memory appear to have significant drawbacks. In particular, expansion of such a manufactured stent in situ would seem to be dependent on the built-in memory intrinsic to a particular polymer composition. There is an obvious danger that the consequent defined expansion may be too little or too much, and it would be evident that this kind of haphazard approach to the treatment of heart conditions would be entirely inappropriate.

According to the present invention, however, such a disadvantage is avoided by providing a stent which can be expanded as necessary in the individual circumstances of a particular patient.

While in a preferred utility of the invention, a stent will be attached to a balloon catheter; the technique of attachment is generally well-known and forms no part of the present invention per se. Merely by way of example, a method for securing a stent to a balloon catheter is described in U.S. Pat. No. 5,860,966 (Tower).

Also, as will be evident from a description of the invention which follows, stents may be adapted for the purposes of drug delivery, nevertheless, use of stents as drug delivery systems is also well-known and does not per se form part of the present invention. Illustrative examples of stents used as drug delivery systems are afforded by U.S. Pat. No. 5,383,928 (Scott et al.), U.S. Pat. No. 5,464,450 (Busceni et al.), U.S. Pat. No. 5,498,238 (Shapland et al.), U.S. Pat. No. 5,554,182 (Dinh et al.), U.S. Pat. No. 5,591,227 (Dinh et al.), U.S. Pat. No. 5,811,447 (Kunz et al.), U.S. Pat. No. 5,843,172 (Yan et al.), U.S. Pat. No. 5,954,706 (Sahatjian), U.S. Pat. No. 5,972,027 (Johnson), 5,980,551 (Summers et al.) and U.S. Pat. No. 6,013,099 (Dinh et al.).

U.S. Pat. No. 4,826,945 (Cohn et al.) describes biodegradable surgical articles made from α-hydroxycarboxylic acid/polyoxyalkylene block copolymers.

Catheters and stents having various geometrical configurations are known, e.g. they may be of hollow cylindrical configuration and additionally be corrugated, or have a circumferentially corrugated or pleated section, see for example U.S. Pat. No. 4,403,985 (Boretos), U.S. Pat. No. 4,784,639 (Patel) and U.S. Pat. No. 5,725,547 (Chuter).

Many polymeric stents/surgical articles require heat curing in situ. The stents/surgical articles of the present invention avoid the necessity for this inconvenient requirement.

The entire contents of the above-mentioned U.S. patents and WO published patent application are incorporated herein by reference.

SUMMARY OF THE INVENTION

The present invention provides a biocompatible non-memory expandable polymeric stent which is at least in part biodegradable and which includes a combination of at least one thermoplastic elastomeric component and at least one thermoplastic non-elastomeric component which has a glass transition temperature above 40° C., the stent being selected from the group of porous stents and stents which have the potential to become porous by action of body fluids in situ, the thermoplastic non-elastomeric component being present in such an amount as will provide mechanical strength and rigidity to the stent when in an expanded mode.

The invention further provides a biocompatible non-memory expandable polymeric article selected from implantable prostheses, catheters other surgical articles and sealants for implantable prostheses, having the polymeric constitution defined in the preceding paragraph for a stent.

The term "non-memory" in the present specification and claims is intended to convey that expansion of the stent or other polymeric article is not due to recovery of a previous shape or size.

DETAILED DESCRIPTION OF THE INVENTION

Figure 1:
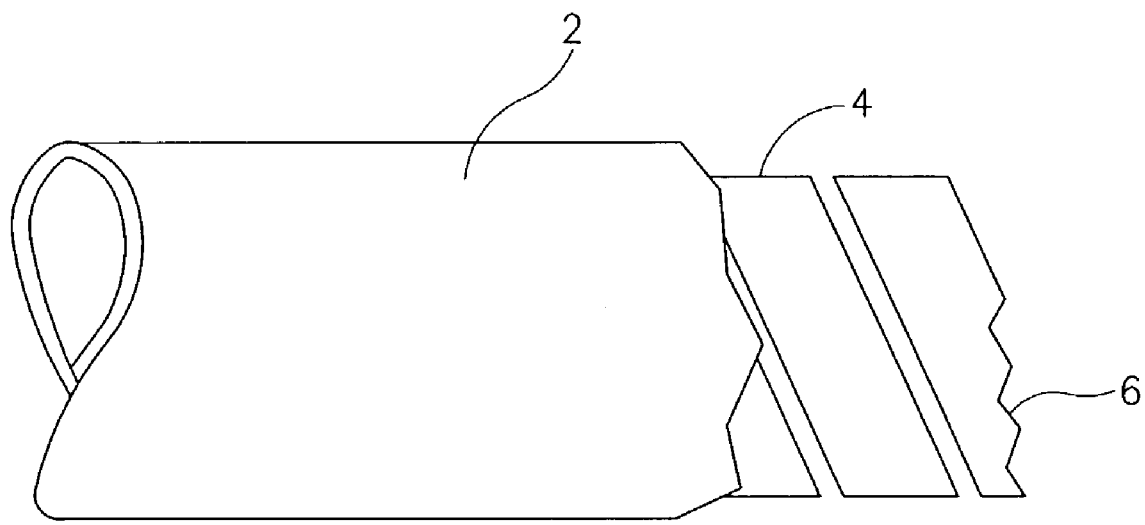
FIG. 1 illustrates an embodiment of a particular configuration for the stent of the invention.

It will be appreciated that the thermoplastic elastomeric components of the stent confer the characteristics of expansion and deformation resulting from the force exerted by the angioplasty balloon when this is inflated, thus allowing the stent to conform with the contours of the lumen, whereas the thermoplastic non-elastomeric components of the stent are responsible for its rigidity and mechanical strength necessary to resist the collapsing force exerted on the stent (and on the lumen) in situ and to prevent any tendency of the stent to revert to its original dimensions after removal of the balloon.

In one embodiment of the invention, the at least one thermoplastic elastomeric component and at least one thermoplastic non-elastomeric component are in integral combination, and in this embodiment, it is preferred that the stent is further characterized by at least one of the following features:
(a) it is adapted for drug delivery in situ;
(b) said thermoplastic elastomeric component includes both hard and soft segments and may comprise a block copolymer;
(c) at least one of the components, preferably the non-elastomeric component, is substantially completely biodegradable;
(d) said combination includes at least one block copolymer containing at least one elastomeric segment as said elastomeric component and at least one non-elastomeric segment as said non-elastomeric component;
(e) the combination includes at least one mixture of at least one elastomeric polymer and at least one non-elastomeric polymer which has a glass transition temperature above 40° C.;
(f) it has a configuration selected from one of the following: (1) an elongated hollow cylindrical configuration; (2) a helical configuration; (3) an elongated hollow cylindrical configuration which encases as an additional mechanical element, a helix formed from at least one biodegradable thermoplastic non-elastomeric polymer which has a glass transition temperature above 40° C.; (4) an elongated hollow cylindrical configuration which is additionally corrugated, or has a circumferentially corrugated or pleated section; (5) an elongated hollow cylindrical configuration having a hole in the cylinder wall remote from either end of the elongated cylinder.

In configuration (5), above, the hole may be circular or oval. The purpose of the hole is that, where a blood vessel branches from another, then the hole may be aligned with the blood flow between a relatively smaller blood vessel, and a relatively larger blood vessel, in which the stent has been inserted.

In the case of a block copolymer, this preferably has a structure selected from $(AB)_n$, ABA and BAB, and ABC (tri-blockcopolymer) where A is said at least one elastomeric segment (soft segment), B is said at least one non-elastomeric segment (hard segment), C is another type of either elastomeric or non-elastomeric segment, and n is an integer of at least one.

In a preferred embodiment of the invention, there is utilized a polymer blend of a thermoplastic elastomeric polymer which has elasticity modulus of <20 Mpa, preferably <10 Mpa, and an elongation of above 50%, preferably >300% and/or a Tg below 37° C. (in the composition) with a thermoplastic non-elastomeric polymer which has a glass transition temperature (Tg) above 40° C. preferably above 37° C. where at least one component, preferably the non-elastomeric component, is biodegradable. The degradation process can take place by a mechanism such as hydrolysis, enzymatic degradation, surface erosion, bulk erosion, dissolution or any combination thereof.

In the polymer blend, the elastomeric and non elastomeric polymers may be selected from amorphous homopolymers, semicrystalline homopolymers, amorphous copolymers, semicrystaline copolymers, block or segmented copolymers of any type of AB, $(AB)_n$, ABA, BAB, ABC branched or graft copolymers, thermoplastic elastomers which contain dendritic structures, plasticized polymers and these can be blended in any combination thereof. The blend can be based on either miscible polymers or on immiscible polymers. When the elastomeric component is a homopolymer its Tg should be below 37° C. preferably below 0° C., and when a thermoplastic block copolymer is used as elastomeric component the Tg of the soft segment should be below 37° C. preferably below 0° C.

In a particular embodiment, a thermoplastic block co-polymer elastomer, e.g. whose soft segment has a Tg below 0° C., may be blended with a thermoplastic non-elastomeric homopolymer which has a Tg above 40° C. preferably above 37° C. For example a thermoplastic segmented elastomer such as a polyurethane with a weight ratio of diisocyanate: chain-extender: soft segment of 2:1:1 respectively can be mixed or blended with poly(L-lactide) which has a Tg above 40° C. e.g. PLLA with an inherent viscosity of 1 to 7. Under loading, upon deformation by inflation of the angioplasty balloon, the elastomeric component, due to its lower Tg and flexibility, is first stressed undergoing deformation and subsequently orientation and crystallization (stress induced crystallization). The orientation and crystallization of the elastomeric component can occur in soft segments of the polyurethane. This can significantly increase the Tg and the rigidity of the polyurethane on the one hand, and phase separation between the polyurethane and PLLA on the other hand. Furthermore, as a result of both deformation and phase separation, an orientation followed by recrystallization of the PLLA can take place. The extent of orientation and recrystallization will be a function of both PLLA content as well as PLLA molecular weight. Recrystallization of the PLLA will subsequently bring about an increase in Tg of the blend including the polyurethane, which may prevent relaxation of the soft segment chains even after the loading is removed and thus lead to a permanent set, while significantly increasing the stiffness as well as the strength of the stent structure. In another embodiment the polymer blend may prepared by blending or mixing a thermoplastic segmented polyurethane which has a high weight ratio of hard segment to soft segment with a PLLA with Tg above 40° C. In the latter combination, under loading upon the deformation, in additional to orientation as well as recrystallization of both soft segment in the polyurethane and PLLA, as described above, an orientation and a semi-crystallization of the hard segment in the polyurethane may also occur. The orientation and semi-crystallization of the hard segment in the polyurethane may impart additional rigidity and strength to the stent structure.

In another embodiment, the polymer blend can be obtained by blending or mixing a thermoplastic elastomeric segmented polyurethane possessing a high weight ratio of hard segment to soft segment, with an amorphous thermoplastic non-elastomeric polylactide such as poly(DL-lactide). The amorphous structure of the PLA along with elasticity of the soft segment in the polyurethane enable the elongation and expansion of the stent to take place more easily. On the other hand, the orientation of the PLA chains along with its high Tg (above 40° C.) prevents polyurethane from undergoing relaxation after the loading is removed. Of course, the orientation and semi-crystallinity of the hard segment of the polyurethane forming the oriented semi-crystalline hard domains can also provide additional rigidity and strength to the stent structure.

Polymers that can be used as elastomeric component in the polymer blend composition are for example: thermoplastic segmented polyurethane, thermoplastic segmented polyurethane urea, thermoplastic segmented polyurethane amide, thermoplastic segmented polyetherester, thermoplastic polydimethylsiloxane, di-block polystyrene polybutadiene, tri-block polystyrene polybutadiene, poly(acrylene ether sulfone)-poly(acryl carbonate) block copolymers, di-block copolymers of polybutadiene and polyisoprene, copolymer of ethylene vinyl acetate (EVA), segmented block co-polystyrene polyethylene oxide, di-block co-polystyrene polyethylene oxide, and tri-block co-polystyrene polyethylene oxide. The non-elastomeric component in the polymer blend can be a synthetic or natural polymer, although synthetics are preferred. Representative synthetic polymers include polyhydroxy acids such as poly(L-lactide), poly(D-lactide), poly(D,L-lactide), poly(glycolide), poly(L-lactide-co-D,L-lactide), poly(L-lactide-co-glycolide), poly(D,L-co-glycolide), poly(1,3-propylenemalonate-co-glycolide), polymalic acid, polydioxanone, poly($\epsilon$-caprolactone), poly(1,3-propylenemalonate-co-lactide), poly(1,3-propylenemalonate-co-dioxanone), polyhydroxybutyrate, polyhydroxyvalerate, polycarbonates, poly(glycolide-co-trimethylene carbonate), poly(glycolide-co-$\beta$-propiolactone), poly(glycolide-co-$\gamma$-butyrolactone), poly(glycolide-co-$\delta$-valerolactone), poly(glycolide-co-$\epsilon$-caprolactone), poly(lactide-cotrimethylenecarbonate), poly(lactide-co-$\beta$-propiolactone), poly(lactide-co-$\gamma$-butyrolactone), poly(lactide-co-$\delta$-valerolactone), poly(lactide-co-$\epsilon$-caprolactone) [O—(CH2)x-O—CO—(CH2)y-OC—]n, where x=1-8 and y=1-8, polyethylene adipate (PEA), polyethylene carboxylates; polyethylene succinate, polyethyleneoxalate, polyethlene subarate, polyethlene azelate, polyethylene sebacate, polytetramethylene carboxylates; polyteteramethylene succinate, polyhexamethylene carboxylates, polydiethylene oxide carboxylates polyanhydrides, polytrimethylene carbonate, polyiminocarbonate, polyethylene carbonate, polypropylene carbonate, polyorthoesters, polyaminoacids, poly(hydroxyalkanoate)s, poly(pseudo amino acids), polyesteramides, and blends and copolymers thereof. Biodegradable natural polymers which can be also used as non-elastomeric component include shellac, polysaccharide such as pectin and polygalactronic acid, alginate and alginic acid, starch, cellulose, guar gum, dextrans, chitosan, chitin, pullulane, polyhyaluronic acids, heparin, proteins such as gelatin, collagen, albumin, zein and modified zein, casein, gluten.

Synthetic gel forming polymers can be also used as a non-elastomeric component. These include polyvinyl alcohols, polyacrylamides, polyvinyl pyrrolidone, polyacrylic acid, polymethacrylic acid, polyacrylates such as polyhydroxy ethyl acrylate, polyhydroxy methyl acrylate, polyhydroxy ethyl methacrylate, polyhydroxy methyl methacrylate and blends and copolymers thereof.

In a particular embodiment, the elatomeric/non-elastomeric polymeric combination useful in the present invention may be constituted by (at least in part) a thermoplastic block-co-polymer. Generally these materials are chemically composed of blocks of two dissimilar homopolymers along the chain backbone. The block copolymers as used herein include A-B diblock structures, A-B-A and ABC triblock polymers, and (AB)n multiblock systems. The nature of the blocks and their sequential arrangement play an important role in determining block copolymer properties. Block lengths in (AB)n polymers are frequently much shorter than those in both di and tri-blockcopolymer (A-B and A-B-A or ABC block copolymers). The term "segment" refers to a particular block or sequence of polymer forming part of the block copolymer. The block copolymers which can be used for construction of the polymeric stent exhibit a two-phase structure. The soft segment or soft block which at service temperature (37° C.) is viscous or rubbery, constitutes the elastomeric component of the polymeric combination of the present invention and the hard segment or hard block which is of a glassy or semicrystalline nature constitutes the non-elastomeric component. The incompatibility between the two blocks or segments leads to phase separation and the creation of hard segment or block domains embedded in the matrix of the soft segment or block. At service temperature (37° C.) the hard domains are either semicrystalline or glassy acting as physical cross-links and/or reinforcing filler particles for the soft segment or block matrix which at the same temperature is in viscous or molten state. The rigid hard domains impart strength, resisting to collapse of the structure and prevent viscous flow, whereas the soft segment or soft block matrix provides high extensibility and flexibility to the system. The hard segment or hard block herein has a Tg above 40° C. preferably above 37° C., whereas the soft segment or soft block Tg is normally well below the use temperature, preferably below 0° C. The elasticity modulus of the block copolymer is below 50 MPa, preferably below 30 MPa. The strength of the block copolymer is above 5 MPa preferably above 20 MPa. The elongation of the block copolymer is above 50% preferably above 100%.

The mechanism of action of the thermoplastic block copolymer stent, like the blend polymer stent, will be through the rigidity and toughness of the stent which are resulted from the orientation and/or semicrystallization of the hard segment or hard block chains, upon the deployment of the stent. The hard segments or hard block should be able to undergo plastic deformation and creeping bringing to orientation and/or semicrystallization of the hard segments or hard block. The latter process will be responsible for preventing relaxation and recovery of the stent after the loading is removed. The extent of orientation is a function of hard segment or hard block content and reflects a change of domain morphology from isolated semi-amorphous to an interconnected semicrystalline microstructure. The longer the hard segment or hard block molecules chain the more the crystallization and better orientation of the hard segment or block and thus more rigidity of the structure can be resulted. Therefore in the case of segmented block copolymer such as thermoplastic polyurethane elastomers, the hard segment should have an enough high molecular weight to undergo plastic deformation and creeping. The weight fraction of the hard segment in the segmented block copolymer should therefore lie in a range between 25% to 50%.

In one embodiment, the composition can be constituted by using a thermoplastic segmented polyetherurethane urea having a hard segment content of 46.5% (wt. %) and polytetramethylene glycol with molecular weight of 2000 as the soft segment. The mechanism of the orientation and/or crystallization process of the hard segment in this segmented polyurethane is as follows; under loading or upon elongation of the polymer the soft segment, due to its lower Tg and flexibility, is first stressed undergoing deformation and subsequently orientation and crystallization. The orientation and crystallization of soft segment can significantly increase the Tg and the rigidity of the polymer in one had and causes better phase separation between two segments on the other hand. The latter process is a primary necessity for crystallization of both soft and hard segments. Furthermore, the local torques, acting through the soft segment, "force strands", cause the long axis of the hard domains to be oriented in the stretch direction, leading to orientation of the individual hard segment transverse to the stretch direction. Further elongation causes hard segments to slip past one another, breaking up the original structure. As elongation continues, hard segments become progressively more oriented into the stretch direction resulting in more rigidity of the structure. To note, this rigidity which resulted from the increase in orientation and crystallization of both segments, is responsible for the permanent set and prevention of the relaxation and recovery after the loading is removed.

Block copolymers are for example: soft segments comprising, but not limited to, oligoethers, such as polytetramethyleneglycol, polypropyleneglycol or polyethyleneglycol, oligoesters, such as polyethyladipate, polycaprolacton, polyethylene succinate, polyethlene subarate, polyethylene sebacate, polytetrametylene succinate, polytetrametylene subarate, polytetrametylene sebacate, copoly(ether-ester), polydimethyl siloxane, polybutadiene, polyisobutylene and hard segments, comprising, but not limited to isocyanates, such as diisocyanate, methylene bis(phenylisocyanate), hexamethylene diisocyanate, cylcohexamethylene diisocyanate, 2,4-toluene diisocyanate, 2,6-toluene diisocyanate or paraphenylene diisocyanate. Chain extender hard segments comprise, but not limited to, ethylene, glycol, butandiol, hexandiol, urea-based chain extenders; water, ethylenediamine or butylenediamine, and polysiloxane-based segments, such as diphenylsiloxane, phenylmethylsiloxane, phenylsesqusiloxane, tetramethyl-p-phenylenesiloxane, tetramethyl-1,4-naphthalenesiloxane, tetramethyl-1,3-tetrafluorophenylenesiloxane, polysiloxane-based blockcopolymers with; alkylene ethers, polysulfone, poly(phenylene oxide), isopropane, styrene, amethylstyrene, bisphenol A carbonate, 9,9-bis-(4-hydroxy-phenyl)fluorene carbonate, tetrabromobisphenol A carbonate, 2,2,4,4,-tetramethyl-1,3,-methylbutylene carbonate, bisphenol A isophthalate, bisphenol A tetraphthalate, hexamethylene tetraphthalate, $_\chi$-benzyl L-glutamate, nylon 6 urethane, urea or imide (as Block A) and methylphenyl siloxane, dimethylsiloxane, diethylsiloxane, or aluminosiloxane (as Block B).

In an alternative embodiment, the stent according to the present invention can be also constructed using an interpenetrating polymer network, IPN, which can be defined as a combination of two polymers in network form, at least one of which is synthesized and/or crosslinked in the immediate presence of the other. An IPN swells but dose not dissolve in solvents. Molecular interpenetration occurs only in the case of total mutual solubility, however, most IPNs phase separate to a greater or lesser extent. Thus molecular interpenetration may be restricted or shared with supermolecular levels of interpenetration. In some cases, true molecular interpenetration is thought to take place only at the phase boundaries. If one polymer is crosslinked and the other is a linear polymer the IPN is called a semi-IPN. Another form of IPN is AB-crosslinked polymer where two polymers are crosslinked to each other forming one network.

In the present invention IPNs can be designed to absorb mechanical energy if one component is a rubbery polymer (low Tg, below the use temperature, preferably below 0° C.) as elastomeric component and the other is a rigid, glassy polymer (non-elastomeric component having a high Tg, above 40° C. preferably above 37° C.).

In one embodiment a semi-IPN based PLLA and silicone can be used as a combination for constructing the polymeric stent. The PLLA is the non-elastomeric component providing support and reinforcement for the silicone, acts as the elastomeric component, which is soft and pliable enabling the expansion of the stent. The combination of these biocompatible polymers yields a structure that is flexible and tough. In this embodiment the IPN are made by reaction of functionalized silicone in the thermoplastic PLLA melt. The silicone reacts to form a thermoset polymer that interpenetrates the thermoplastic. The silicone and PLLA can be injection molded and react to form the IPN in the mold. In another embodiment thermoplastic polyurethane can be used as the linear elastomeric component and polyacrylamide as the thermoset non-elastomeric component in the IPN. The polymerization and simultaneously crosslinking of acrylamide occur in the thermoplastic linear polyurethane matrix. This can be done by preswelling the polyurethane by solution of acrylamide, crosslinker and initiator and then polymerization which can be carried out by exposing the matrix to heat or UV-irritation. A homo-IPN can also be used for construction of the stent. One relevant example for homo-IPN can be the system constituted of polyurethane/polyurethane. A polyurethane with a low ratio of hard to soft segment can be used as a thermoset elastomeric component whereas a polyurethane possessing a high ratio of hard to soft segment as a linear thermoplastic non-elastomeric component.

Polymers that can be used as elastomeric component in the IPNs composition are for example; silicones, polyetherurethane, polyetherurethaneurea, polyetherurethneamide, polyesterurethane, polyesterurethaneurea, polyesterurethaneamide, polyisobutylene, polyisoprene, polybitadiene and other polymers like those which can be used in the blend composition as the elastomeric component.

The polymers which can be used as the non-elastomeric component in the IPNs composition include the polymers that can be used in the blend composition as the non-elastomeric component. The IPN can be constituted as either full IPN, homo-IPN, semi-IPN, latex IPN or AB-crosslinked polymer. In the case of the semi-IPN the non-linear thermoset polymer can be either elastomeric component or non-elastomeric component.

The stent of the invention may be used as a drug delivery system for e.g. restenosis-preventing drugs. Suitable drugs will usually be incorporated within the interstices and/or on the surface of the polymers, and would generally be released after the stent is positioned in the lumen by diffusion of the active materials and/or biodegradation of the polymers. Exemplary suitable drugs, and their mode of carriage by the stent as well as their delivery, are described in the U.S. patents mentioned above and incorporated by reference herein.

As previously implied, the stents are intrinsically porous by design, or alternatively or additionally they have the potential to become porous by action of body fluids in situ. This existing or induced porosity may be of importance for absorption and delivery of drugs, but it is of especial importance for encouraging ingrowth of neointimal and endothilial tissues.

While any known feasible configuration for the stent is within the compass of this invention, the stent may have for example a hollow cylindrical configuration or a helical configuration. Optionally, the stent having a hollow cylindrical configuration may encase as an additional mechanical element, a helix formed from at least one biodegradable thermoplastic non-elastomeric polymer which has a glass transition temperature above 40° C.

In another embodiment of the invention, the stent consists of at least two discrete mechanical elements, at least one of which is formed from such at least one thermoplastic elastomeric component and at least one of which is formed from such at least one thermoplastic non-elastomeric component. In this embodiment, the stent may be further characterized by at least one of the following features: (a) at least one of the discrete elements is adapted for drug delivery in situ; (b) the thermoplastic elastomeric component includes both hard and soft segments and may comprise a block copolymer; (c) at least one of the discrete elements is substantially completely biodegradable.

In this embodiment of the invention, the stent preferably includes a first mechanical element of hollow cylindrical configuration, formed from the elastomeric polymer, and a second mechanical element of helical configuration formed from the non-elastomeric polymer which is biodegradable and is adapted to be encased within the first mechanical element. The first mechanical element is preferably adapted for drug delivery in situ.

Referring now to FIG. 1, this illustrates a configuration according to the invention, where hollow cylindrical element 2 is depicted in cutaway form to reveal helical element 4—terminated schematically at 6—inserted within the cylindrical element. As previously mentioned, element 2 is formed either from the inventive integral combination of elastomeric and thermoplastic non-elastomeric components, or merely from elastomeric polymer, while element 4 is formed from at least one biodegradable thermoplastic non-elastomeric polymer which has a glass transition temperature above 40° C. In this type of embodiment, inflation of the angioplasty balloon encase in the helix and the hollow cylinder exerts outwards radial pressure on the circumference of both the helix and the hollow cylinder. The helix supplies the necessary mechanical support at the lumen surface (when the hollow cylinder is solely elastomeric) or supplements this support where the hollow cylinder includes the integral combination of both elastomeric and thermoplastic non-elastomeric components. A two-part stent assembly of this type can be adapted for drug delivery from the outer surface and/or interstices of the hollow cylinder, and/or from the helix as this biodegrades.

Figure 2:
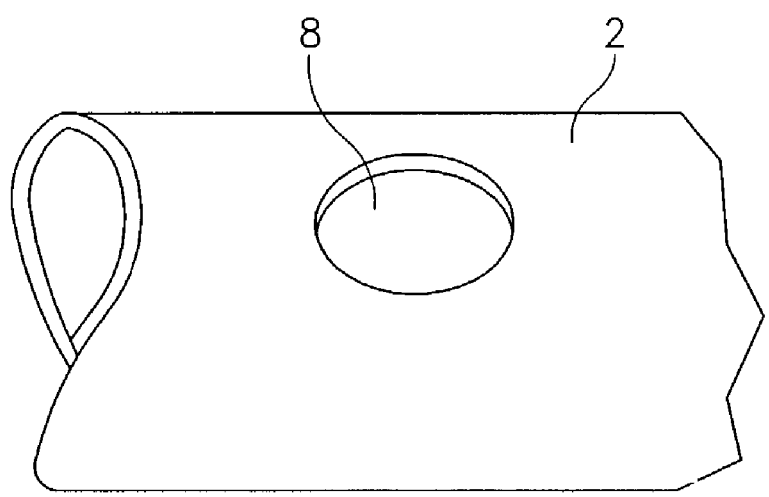
FIG. 2 illustrates an embodiment of a different configuration for the stent of the invention.

FIG. 2 illustrates an embodiment of the invention in which the cylindrical stent 2 is pierced by a circular hole 8, for the purpose of alignment with a branching blood vessel opening, as explained above.

Figure 5:
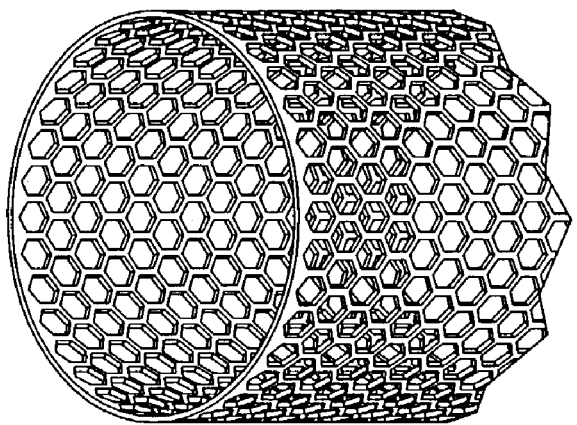
FIGS. 3-5 illustrate, respectively, different open-mesh embodiments for the stent of the invention.
Figure 4:
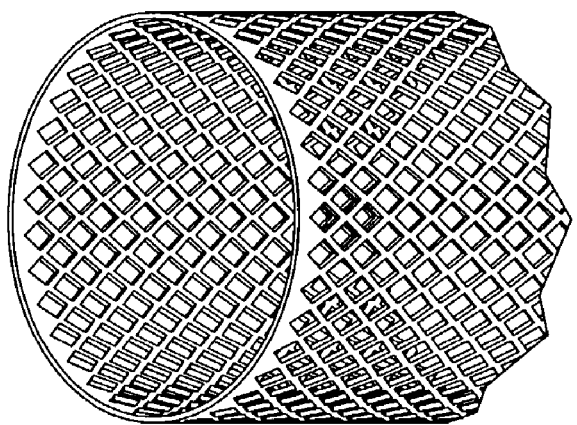
Figure 3:
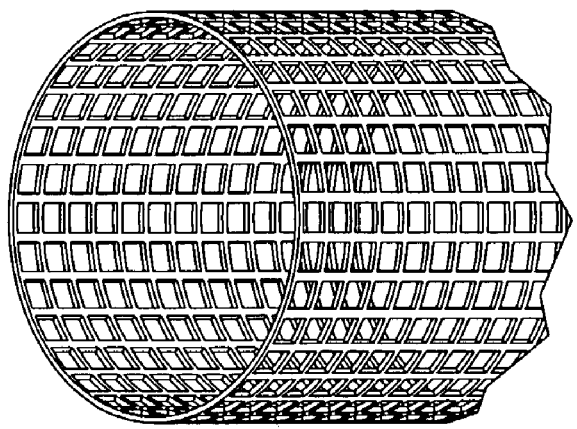

It will be appreciated that the polymeric article of the invention, and in particular the polymeric stent of the invention, is, of course, not limited in its configuration to the embodiments illustrated in FIG. 1 and FIG. 2, but can be made essentially in any useful configuration, which as a practical matter may be applied for its intended purpose. Thus, by way of further exemplification, instead of being a solid cylindrical surface, the polymeric stent may have an open structure in the form of a mesh. Illustrative examples are shown in FIGS. 3, 4 and 5, depicting respectively a square, diamond-shaped and hexagonal mesh surface. The mesh thicknesses are not necessarily drawn to scale, and it will evidently be within the competence of a person skilled in the art to construct the polymeric stent or other article of the invention in such a manner as to impart to it the necessary balance between rigidity and flexibility. Among the advantages of a stent or other article having a mesh-type surface, there may be mentioned, e.g., relatively free flow of blood at blood vessel junctions.

The stents are utilized in a manner which in principle is largely known. Thus, for example, it will be apparent to a person of the art that there may be utilized a balloon mounted on a balloon catheter incorporating device for inflating and deflating the balloon, with a stent of the invention mounted over the balloon in its deflated mode and frictionally engaging the deflated balloon.

There will now be described illustrative examples of the combination, according to the invention, of elastomeric and thermoplastic non-elastomeric components.

EXAMPLE I

50:50 Blend of Polyetherurethane (elastomeric) with Poly-L-lactic Acid (non-elastomeric).

Materials: The polyetherurethane (PEU) was prepared by reacting polytetramethyleneglycol (soft segment; MW 2000 with methylene bis(phenylisocyanate), followed by reaction of the initial product with butanediol as chain extender. The molar ratio of these reactants was 1:2:1. Poly-L-lactic Acid (PLLA) had a MW 2000 and Tg 30-45° C. Dimethylacetamide (DMA) was used as solvent.

Method: PEU (I g) and PLLA (I g) were mixed with DMA (40 ml) at 60° C., using a magnetic stirrer, until complete dissolution of the polymers, giving a transparent solution, was achieved. A film of the polymer blend was prepared after casting the solution and evaporation of the solvent at 60° C. in an oven overnight. The film was subsequently dried at 40-50° C. under vacuum for a further 16 hours. The resulting film was semi-transparent which changed to an opaque white milky film when it was stressed and loaded.

EXAMPLE II

75:25 Blend of Polyetherurethane (elastomeric) with Poly-L-lactic Acid (non-elastomeric).

Materials: The polyetherurethane (PEU) was prepared by reacting polytetramethyleneglycol (soft segment; MW 2000 with methylene bis(phenylisocyanate), followed by reaction of the initial product with butanediol as chain extender. The molar ratio of these reactants was 1:2:1. Poly-L-lactic Acid (PLLA) had a MW 2000 and Tg 30-45° C. Dimethylacetamide (DMA) was used as solvent.

Method: PEU (1.5 g) and PLLA (0.5 g) were mixed with DMA (40 ml) at 60° C., using a magnetic stirrer, until complete dissolution of the polymers, giving a transparent solution, was achieved. A film of the polymer blend was prepared and subsequently subjected to the same procedure as in Example 1. The resulting film was semi-transparent which changed to an opaque white milky film when it was stressed and loaded, but the product was less flexible and harder than the product of Example I.

EXAMPLE III

50:50 Blend of Polyetherurethane (elastomeric) with Poly-DL-lactic Acid (non-elastomeric). Materials: The polyetherurethane (PEU) was prepared by reacting polytetramethyleneglycol (soft segment; MW 2000 with methylene bis (phenylisocyanate), followed by reaction of the initial product with butanediol as chain extender. The molar ratio of these reactants was 1:2:1. Poly-DL-lactic Acid (PDLLA) had a MW 2000 and Tg 30-45° C. Dimethylacetamide (DMA) was used as solvent.

Method: PEU (1.3 g) and PDLLA (0.7 g) were mixed with DMA (40 ml) at 60° C., using a magnetic stirrer, until complete dissolution of the polymers, giving a transparent solution, was achieved. A film of the polymer blend was prepared and subsequently subjected to the same procedure as in Example 1. The resulting film was semi-transparent which changed to an opaque white milky film when it was stressed and loaded.

EXAMPLE IV

50:50 Blend of Polyesterurethane (elastomeric) with Poly-L-lactic Acid (non-elastomeric).

Materials: The polyesterurethane (PEsU) was prepared by reacting polyethyleneadipate (soft segment; MW 2000 with methylene bis(phenylisocyanate), followed by reaction of the initial product with butanediol as chain extender. The molar ratio of these reactants was 1:2:1. Poly-L-lactic Acid (PLLA) had a MW 2000 and Tg 30-45° C. Dimethylacetamide (DMA) was used as solvent.

Method: PEsU (I g) and PLLA (1 g) were mixed with DMA (40 ml) at 60° C., using a magnetic stirrer, until complete dissolution of the polymers, giving a transparent solution, was achieved. A film of the polymer blend was prepared and subsequently subjected to the same procedure as in Example 1. The resulting film was semi-transparent which changed to an opaque white milky film when it was stressed and loaded. This film was more rigid and harder than the products of Examples I-III.

EXAMPLE V

50:50 Blend of Polyetherurethane/Cycloaliphatic Diisocyanate (elastomeric polymer) with Poly-L-lactic Acid (non-elastomeric polymer).

Materials: The elastomer ("PEU") was Tecoflex EG-80A-B20 (polyetherurethane with a cycloaliphatic diisocyanate i.e. cyclohexane diisocyanate, HMDI) supplied by Thermedics. The non-elastomer poly-L-lactic acid (PLLA) had a MW about 57,000 and Tg 45-60° C. Chloroform was used as solvent.

Method: PEU (1 g) and PLLA (1 g) were dissolved separately in 20 ml chloroform at room temperature using a magnetic stirrer until the polymers dissolved completely, and the solutions were mixed together. The resulting solution was poured into a Petri dish and the solvent was allowed to evaporate at room temperature. A film of the polymer blend was obtained and subsequently dried under vacuum at 40-50° C. for 16 hours, to give an opaque, milky-white film.

EXAMPLES VI-IX

When Example V was repeated using PEU:PLLA blends in a 60:40, 70:30, 80:20 or 90:10 ratio, the product in all cases was an opaque, milky-white film.

EXAMPLES X-XIV

When Examples V-IX were repeated, but substituting Tecoflex EG-85A-B20 for the Tecoflex EG-80A-B20, the product in all cases was an opaque, milky-white film.

EXAMPLES XV-XIX

When Examples V-IX were repeated, but substituting Tecoflex EG-93A-B20 for the Tecoflex EG-80A-B20, the product in all cases was an opaque, milky-white film.

EXAMPLES XX-XXIV

When Examples V-IX were repeated, but substituting PLLA of MW about 164,000 for the PLLA of MW about 57,000, the product in all cases was an opaque, milky-white film.

EXAMPLES XXV-XXX

When Example V was repeated, but using 40:60, 50:50, 60:40, 70:30, 80:20 and 90:10 blends of PEU which was Tecoflex EG-80A-B20 from Thermedics and PLLA of MW about 2000, the product in all cases was an opaque, milky-white film.

EXAMPLES XXXI-XXXVI

When Example V was repeated, but using 40:60, 50:50, 60:40, 70:30, 80:20 and 90:10 blends of PEU which was Tecoflex EG85A-B20 from Thermedics and PLLA of MW about 2000, the product in all cases was an opaque, milky-white film.

EXAMPLES XXXVII-XLII

When Example V was repeated, but using 40:60, 50:50, 60:40, 70:30, 80:20 and 90:10 blends of PEU which was Tecoflex EG-93A-B20 from Thermedics and PLLA of MW about 2000, the product in all cases was an opaque, milky-white film.

EXAMPLES XLIII-XLVII

When Example V was repeated, but using 50:50, 60:40, 70:30, 80:20 and 90:10 blends of PEU which was Tecoflex EG-85A-B20 from Thermedics and PLLA of MW about 164,000, the product in all cases was an opaque, milky-white film.

While particular embodiments of the invention have been particularly described hereinabove, it will be appreciated that the present invention is not limited thereto, since as will be readily apparent to skilled persons, many modifications or variations can be made. Such modifications or variations which have not been detailed herein are deemed to be obvious equivalents of the present invention.

The invention claimed is:

1. A biocompatible non-memory expandable polymeric stent containing one helical element only and a hollow cylindrical element, wherein said helical element is adapted to be encased within the hollow part of said cylindrical element, and wherein said stent is adapted to be positioned in a body lumen, is at least in part biodegradable and includes a combination of at least one thermoplastic elastomeric polymer and at least one thermoplastic non-elastomeric polymer that has a glass transition temperature greater than 40° C., said stent being selected from the group of porous stents and stents that have a potential to become porous by action of body fluids in situ, said thermoplastic non-elastomeric polymer being present in such an amount as will provide mechanical strength and rigidity to the stent when in an expanded mode, and wherein said hollow cylindrical element is formed from said elastomeric polymer, and said one helical element is formed from said non-elastomeric polymer that is substantially biodegradable and said stent is adapted to provide necessary mechanical support at the lumen surface.

2. A stent according to claim 1, further characterized by at least one of:
   at least one of said discrete elements is adapted for drug delivery in situ;
   said thermoplastic elastomeric polymer includes hard and soft segments and optionally comprises a block copolymer;
   said hollow cylindrical element is also substantially biodegradable.

3. A stent according to claim 1, wherein said thermoplastic elastomeric polymer includes hard and soft segments and comprises a block copolymer which has a structure selected from the group consisting of $(AB)_n$, $(AB)_nA$, $B(AB)_n$ and ABC, where A is said at least one elastomeric segment, B is said at least one non-elastomeric segment, C is a different elastomeric or non-elastomeric segment, and n is a predetermined integer greater than or equal to one.

* * * * *